United States Patent [19]
Kupfer et al.

[11] Patent Number: 6,040,152
[45] Date of Patent: *Mar. 21, 2000

[54] METHOD AND ASSAY FOR REGULATION OF T CELL PROLIFERATION

[75] Inventors: Abraham Kupfer; Hannah Kupfer, both of Denver; Colin R. F. Monks, Idaho Springs, all of Colo.

[73] Assignee: National Jewish Medical and Research Center, Denver, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/775,310

[22] Filed: Dec. 31, 1996

[51] Int. Cl.⁷ .................................................. C12Q 1/02
[52] U.S. Cl. ........................ 435/29; 435/7.1; 435/7.24; 435/325
[58] Field of Search ....................... 435/7.24, 29, 325, 435/7.1

[56] References Cited

U.S. PATENT DOCUMENTS

| | | |
|---|---|---|
| 4,937,232 | 6/1990 | Bell et al. . |
| 5,432,076 | 7/1995 | Rudd et al. . |
| 5,474,897 | 12/1995 | Weiss et al. . |
| 5,552,396 | 9/1996 | Heath, Jr. et al. . |

OTHER PUBLICATIONS

Baier et al., 1994, *Eur. J. Biochem.,* 225:195–203.
Baier et al., 1993, *J. of Biolog. Chemistry,* 268(7):4997–5004.
Hug et al., 1993, *Biochem.,* 291:329–343.
Mochly–Rosen, 1995, *Science,* 268:247–251.
Weiss et al., 1994, *Cell,* 76:263–274.
Yamada et al., 1995, *Biochem. J.,* 308:177–180.
Meller et al., Molecular and Cellular Biology, vol. 16, 5782–5791, Oct. 1996.
Baier–Bitterlich et al., Molecular and Cellular Biology, vol. 16, 1842–1850, Apr. 1996.
Kupfer et al. J. Exp. Med., vol. 179: 1507–1514, May 1994.

*Primary Examiner*—Christina Y. Chan
*Assistant Examiner*—Patrick J. Nolan
*Attorney, Agent, or Firm*—Sheridan Ross, P.C.

[57] ABSTRACT

The present invention discloses a method to regulate T cell proliferation by regulating protein kinase C theta (PKCθ) in a T cell. Also disclosed are assays for evaluating the ability of a T cell to proliferate in response to an antigen-specific stimulus, a method to regulate T cell proliferation in a mammal in vivo, a method to identify compounds which regulate T cell proliferation, and compounds identified thereby.

12 Claims, No Drawings

METHOD AND ASSAY FOR REGULATION OF T CELL PROLIFERATION

GOVERNMENT RIGHTS

This invention was made in part with government support under AI23764, awarded by the National Institutes of Health. The government has certain rights to this invention.

FIELD OF THE INVENTION

The present invention generally relates to a method to regulate protein kinase C theta. More particularly, the present invention relates to an assay for T cell proliferation and a method to regulate T cell proliferation.

BACKGROUND OF THE INVENTION

Stimulation of a T cell through its T cell receptor (TCR), in conjunction with appropriate costimulatory signals, results in complex cascades of signal transduction events within the T cell that eventually lead to T cell proliferation, differentiation and cytokine production. Although many cellular signaling molecules have been causally related to the various endpoints of T cell activation, the understanding of the detailed intermolecular connections between signaling events is still evolving. The study of various protein kinases is at the forefront of this evolving knowledge.

Multiple families of protein-kinases are present in each cell. The same cell may express several, structurally-related yet genetically distinct, kinases of each family. The activity of the family of serine/threonine protein kinase C (PKC) enzymes has been implicated in T-cell activation. Until the present invention, however, it was unknown which members of the PKC-family regulate the various T cell responses to foreign antigens.

A variety of assays have been used to evaluate the ability of T cells to be activated in vitro and to make predictions about the ability of such T cells to proliferate and/or produce cytokines in vivo. Such methods for measuring T cell activation, however, often involve the use of "immortalized" cells (e.g., hybridomas) or antibodies (as artificial stimulators of the T cell), which may not accurately reflect a normal T cell response in vitro or in vivo. Therefore, there is a need for a system for evaluating antigen-specific T cell activation which can be used as a predictor of and/or regulatory target for T cell activation in vivo.

SUMMARY OF THE INVENTION

One embodiment of the present invention includes a method to regulate T cell proliferation by regulating protein kinase C theta (PKCθ) in a T cell. The method includes regulating PKCθ by degrading PKCθ, binding a regulatory compound to PKCθ, regulating transcription of PKCθ, regulating translation of PKCθ, altering the phosphorylation state of PKCθ, or regulating the interaction of PKCθ with another signal transduction molecule. Regulation of PKCθ can include up regulation or down regulation of PKCθ. In some embodiments, regulation of PKCθ can be performed in vivo or ex vivo. In a further embodiment, regulation of PKCθ includes administering to a T cell a regulatory compound which down regulates PKCθ.

Another embodiment of the present invention relates to an assay for evaluating the ability of a T cell to proliferate in response to an antigen-specific stimulus. The method includes the steps of culturing a T cell having a T cell receptor with an antigen presenting cell having an MHC-antigen complex, and determining whether PKCθ is activated in the T cell. The step of determining whether PKCθ is activated in the T cell can include techniques such as determining an increase in the level of PKCθ expression compared to the level of PKCθ in a resting T cell, determining whether PKCθ translocates to the site of contact between the T cell receptor and the MHC-antigen complex, and determining whether PKCθ is enzymatically active. In one embodiment, immunofluorescent microscopy is used to determine whether PKCθ translocates. In another embodiment, a kinase assay is used to determine whether PKCθ is enzymatically active.

Yet another embodiment of the present invention relates to a method to identify a regulatory compound which regulates T cell proliferation. The method includes the steps of (a) culturing a T cell having a T cell receptor with an antigen presenting cell having an MHC-antigen complex wherein the T cell receptor binds to the MHC-antigen complex to form an antigen-specific site of contact between the T cell and the antigen presenting cell; (b) contacting the T cell with a putative regulatory compound under conditions in which, in the absence of the putative regulatory compound, PKCθ is activated in the T cell; and (c) assessing the ability of the putative regulatory compound to regulate PKCθ in the T cell, wherein a change in a characteristic of PKCθ activity in the presence of the putative regulatory compound compared to in the absence of the putative regulatory compound indicates that the compound is able to regulate antigen-specific T cell proliferation.

Another embodiment of the present invention relates to a method to regulate T cell proliferation in a mammal in vivo by administering to a mammal a regulatory compound which regulates PKCθ. In a further embodiment, the regulatory compound is administered to the mammal with a pharmaceutically acceptable carrier. In a preferred embodiment, the regulatory compound down regulates PKCθ. This method is useful for treating a mammal with a disease which includes immunoproliferative disease, autoimmune disease, graft-versus-host disease, and allergic disease. This method is also useful for treating a mammal which has received a transplant.

Yet another embodiment of the present invention relates to a regulatory compound which regulates PKCθ in a T cell. Such a compound is characterized by its ability to regulate PKCθ by regulating the production of PKCθ, by regulating the ability of PKCθ to translocate to a site of contact between a T cell receptor on the T cell and an MHC-antigen complex on an antigen presenting cell, or by regulating the enzymatic activity of PKCθ.

A further embodiment of the present invention relates to a method to identify a compound which regulates PKCθ. The method includes the steps of (a) contacting a cell having a PKCθ signal transduction pathway with a putative regulatory compound and a stimulator, under conditions in which, in the absence of the putative regulatory compound, the stimulator initiates the PKCθ signal transduction pathway such that PKCθ is activated; and (b) assessing the ability of the putative regulatory compound to regulate the PKCθ signal transduction pathway, wherein a change in a characteristic of PKCθ activity in the cell in the presence of the putative regulatory compound compared to in the absence of the putative regulatory compound indicates that the compound is able to regulate PKCθ.

DETAILED DESCRIPTION OF THE INVENTION

The present invention relates to the discovery that a single isoform of protein kinase C (PKC), protein kinase C theta (PKCθ), regulates antigen-specific T cell proliferation. Specifically, the present invention relates to the regulation of PKCθ in order to regulate T cell proliferation.

The activation of T cells by antigen presenting cells (APCs) is spatially restricted to the site of T cell-APC contact, where receptors on the T cells engage their counter receptors on the APCs. The present inventors used this localized engagement to identify, at the single cell level, intracellular proteins involved in the T cell activation process. The present inventors have unexpectedly found that, of the six known isoforms of protein kinase C (PKC) in antigen specific T cell clones activated by APCs, only protein kinase C theta (PKCθ) translocated to (i.e., clustered at) the site of cell contact. Accordingly, in vitro kinase assays of PKC-immunoprecipitates from the T cell-APC conjugates showed a selective increase in the activity of PKCθ, indicating that the translocated enzyme is active. Several modes of partial T cell activation that failed to cause PKCθ translocation also failed to cause T cell proliferation, further demonstrating the involvement of PKCθ in T cell activation, and in particular, T cell proliferation. The experimental work supporting these observations is discussed in detail in the Examples section below.

PKCθ is a calcium-independent isoform of the PKC family of serine-threonine kinases. The PKC isoenzymes play an important role in many cell signaling events. PKCθ shares a high sequence homology with PKCδ, but its function was previously unknown. Unlike the other PKC isoforms, PKCθ has limited tissue distribution and has been reported to be predominantly expressed in hematopoietic cells and in skeletal muscle. Cell fractionation analysis of skeletal muscle indicates that, upon treatment with either phorbol myristate acetate (PMA) or insulin, PKCθ becomes membrane-associated, like all other tested PKC isoforms. Similar results are achieved with PMA activation of Jurkat T cells. Thus, with the exception of its selective expression, neither analysis of PKCθ's primary structure nor biochemical studies have previously indicated a unique role for PKCθ in either skeletal muscle or T cells.

One embodiment of the present invention relates to a method to regulate T cell proliferation by regulating PKCθ in a T cell. According to the present invention, "regulating PKCθ" refers to specifically regulating the PKCθ molecule or to regulating the PKCθ signal transduction pathway. As used herein, the term "regulate" or regulating can be used interchangeably with the term "modulate". To "regulate" a molecule, a pathway, or a function of PKCθ or a PKCθ signal transduction pathway in the present invention refers to specifically controlling, or influencing the activity of such a molecule, pathway, or function, and can include regulation by activation, stimulation, inhibition, alteration or modification of such molecule, pathway or function. Thus, PKCθ regulation can include up regulating or down regulating PKCθ. As used herein, the term "up regulating PKCθ" refers to an action that ultimately results in an increase in T cell proliferation and/or other signal transduction events in a signal transduction pathway mediated by PKCθ. In addition, the term "down regulating PKCθ" refers to an action that ultimately results in a decrease in T cell proliferation and/or other signal transduction events in a signal transduction pathway mediated by PKCθ.

The ability to specifically regulate T cell proliferation is particularly useful as a therapeutic technique. For example, many diseases can potentially be ameliorated by down regulation of T cell proliferation. Examples of such diseases include, but are not limited to, immunoproliferative disease, autoimmune disease, graft-versus-host disease, or allergic disease. In addition, recipients of transplants, such as organ transplants, typically require immunosuppression. Alternatively, the ability to up regulate T cell proliferation is useful to ameliorate diseases, or conditions, such as immunodeficiency diseases or cancer.

According to the present invention, "PKCθ" refers to known PKCθ proteins. PKCθ can also refer to proteins encoded by allelic variants that have a similar, but not identical, nucleic acid sequence to naturally occurring, or wild-type, sequences. An allelic variant is a gene that occurs at essentially the same locus (or loci) in the genome as the PKCθ gene, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

It is to be appreciated that the present invention also includes mimetopes of PKCθ proteins that can be used in accordance with methods as disclosed for PKCθ protein of the present invention. As used herein, a mimetope of a PKCθ protein refers to any compound that is able to mimic the activity of such a PKCθ protein, often because the mimetope has a structure that mimics the PKCθ protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway.

As used herein, the phrase "signal transduction pathway" or "signal transduction event" refers to at least one biochemical reaction, but more commonly a series of biochemical reactions, which result from interaction of a cell with a stimulatory compound. Thus, the interaction of a stimulatory compound with a cell generates a "signal" that is transmitted through the signal transduction pathway, ultimately resulting in a cellular response.

A signal transduction pathway refers to the biochemical relationship between a variety of signal transduction molecules that play a role in the transmission of a signal from one portion of a cell to another portion of a cell. Signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. An example of a "cell surface receptor" of the present invention is the T cell receptor (TCR). As used herein, the phrase "intracellular signal transduction molecule" includes those molecules or complexes of molecules involved in transmitting a signal from the plasma membrane of a cell through the cytoplasm of the cell, and in some instances, into the cell's nucleus. In the present invention, PKCθ is an "intracellular signal transduction molecule", but can also be referred to as a "signal transduction molecule".

A signal transduction pathway in a cell can be initiated by interaction of a cell with a stimulator that is inside or outside of the cell. If an exterior (i.e. outside of the cell) stimulator (e.g., an MHC-antigen complex on an antigen presenting cell) interacts with a cell surface receptor (e.g., a T cell receptor), a signal transduction pathway can transmit a signal across the cell's membrane, through the cytoplasm of the cell (e.g., through translocation of PKCθ), and in some instances into the nucleus. If an interior (e.g. inside the cell) stimulator interacts with an intracellular signal transduction molecule, a signal transduction pathway can result in transmission of a signal through the cell's cytoplasm, and in some instances into the cell's nucleus.

Signal transduction can occur through: the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Typically, signal transduction occurs through phosphorylating a signal transduction molecule including PKCθ. According to the present invention, all the signal transduction molecules of the PKCθ signal transduction pathway need not be known in order to successfully utilize the methods of the present invention. According to the present invention, a PKCθ signal transduction pathway refers generally to a pathway in which PKCθ protein regulates a pathway that includes engaged-receptors, PKC-substrates and/or RACKs (receptors for activated C kinase).

Regulation of PKCθ can be accomplished by a mode of regulation including regulation of the production of PKCθ (e.g., gene or protein expression); by regulation of the physical location of the PKCθ molecule, such as by regulating the translocation of the molecule to the membrane; or by regulating the enzymatic activity of PKCθ (i.e., regulating the activation or the function of PKCθ, such as by preventing activation of PKCθ or deactivating PKCθ that is activated).

Techniques or methods by which one or more of the above modes of regulation of PKCθ can be accomplished include, but are not limited to, (a) degrading PKCθ, (b) binding a regulatory compound to PKCθ, (c) regulating transcription of PKCθ, (d) regulating translation of PKCθ, (e) altering the phosphorylation state of PKCθ or a molecule which interacts with PKCθ (e.g., dephosphorylating, preventing phosphorylation of, or phosphorylating PKCθ and/or a molecule with which PKCθ interacts), and (f) regulating the interaction of PKCθ with another signal transduction molecule (e.g., by physically blocking the interaction between two molecules or by moving one molecule relative to the other such that interaction between the two can not occur).

In one embodiment of the present invention, PKCθ is regulated by administration of a regulatory compound that inhibits PKCθ such that T cell proliferation is inhibited. Such a regulatory compound can regulate PKCθ by any of the above-mentioned techniques for regulating PKCθ, such as by binding to PKCθ. Such compounds can be known compounds, such as known protein kinase C inhibitors or known proteases or compounds identified by the methods for identifying a compound which regulates PKCθ and/or T cell proliferation as discussed in detail below.

In one embodiment of the present invention, PKCθ is regulated in vivo in a mammal. In another embodiment, PKCθ is regulated ex vivo in a mammal. As used herein, in vivo refers to regulating PKCθ directly in a mammal, such as by administering a regulatory compound directly to a living mammal. Ex vivo refers to regulating PKCθ in a mammal by performing at least part of the regulatory step outside of the mammal, such as by contacting a population of cells removed from a mammal with a regulatory compound under conditions such that the regulatory compound interacts with targeted cell types (i.e., T cells) and returning the contacted cells to the mammal. In vivo or ex vivo regulation of PKCθ can be useful, for example, for ameliorating any of the diseases described above for which regulation of T cell proliferation is desirable.

Another embodiment of the present invention relates to an assay for evaluating the ability of a T cell to proliferate in response to an antigen-specific stimulus. Such an assay includes the steps of (a) culturing a T cell having a T cell receptor (TCR) with an antigen presenting cell having an MHC-antigen complex, and (b) determining whether PKCθ is activated in the T cell. If the T cell has a T cell receptor which binds to, or recognizes, the MHC-antigen complex on the antigen presenting cell, a T cell-APC conjugate is formed. The binding of a T cell receptor to an MHC-antigen complex forms a site or point of contact between the T cell and the antigen presenting cell. Such a site of contact between a T cell and an antigen presenting cell is an antigen-specific interaction, as opposed to a random cell-cell contact. As a result of this antigen-specific interaction, PKCθ is activated in the T cell and translocates to the site of contact, thus indicating that the T cell has been activated and can proliferate. If no antigen-specific site of contact is formed, PKCθ will not be activated and will not translocate to the site of contact, therefore indicating that the T cell is not activated and will not proliferate. Using such an assay of the present invention is an extremely sensitive and useful method for evaluating the ability of a T cell to proliferate in response to an antigen-specific stimulus. For example, such an assay can be used to identify the antigen that is recognized by a particular T cell, to identify a T cell that recognizes a particular antigen, to evaluate the effects of modifying culture conditions on a known T cell-antigen interaction, or to evaluate the effects of any other manipulations on a T cell-antigen interaction. In addition, such an assay can be a valuable tool for investigating PKCθ signal transduction events in any cell, and particularly, a T cell.

According to the present invention, a suitable T cell for use in a method or an assay of the present invention is, minimally, a T cell (i.e., T lymphocyte) which has a T cell receptor (TCR) and a PKCθ signal transduction pathway which, when activated, will effect proliferation of the T cell. In particular, suitable T cells for use in any of the methods or assays of the present invention include any T cell that has a PKCθ signal transduction pathway in which PKCθ is translocated to the antigen-specific site of contact between the T cell receptor on the T cell and an MHC-antigen complex on an antigen presenting cell. Such cells can include normal T cells (e.g., primary lymph node T cells, primary splenic T cells, or T cells from TCR-transgenic mice), T cell lines and T cell clones. A suitable T cell for use in the present invention can also include genetically engineered T cells, such as recombinant cells that have been transformed with, for example, a recombinant molecule encoding PKCθ and/or a PKCθ transcription indicator recombinant molecule, providing that such a recombinant cell includes all of the signal transduction pathways necessary to regulate T cell proliferation in a T cell.

Activated T cell hybridomas produce cytokines but fail to proliferate and later undergo apoptosis. In addition, the present inventors have unexpectedly discovered that PKCθ is not translocated in APC-activated T cell hybridomas. T cell hybridomas differ from normal T cells (e.g., primary T cells or T cell clones) in their activation requirements. For example, hybridomas do not depend on antigen-specific stimulation to proliferate, and in fact, many hybridomas lose their antigen specificity altogether. Therefore, the inability of T cell hybridomas to activate PKCθ demonstrates that PKCθ participates in the induction of an antigen-specific T cell response. As such, a suitable T cell for use in a method or assay of the present invention typically does not include T cell hybridomas, unless, for example, such T cell hybridomas express recombinant PKCθ that can be activated. Techniques for production of such a recombinant molecule are described in detail below.

According to the present invention, a T cell receptor (TCR), as described herein, specifically refers to the antigen receptor of a T cell. It is recognized in the art that there are a variety of other receptors expressed by a T cell which are important in T cell responses and which may be involved in the activation of PKCθ, including, but not limited to, CD3, CD4, CD8, CD28, CTLA-4, CD45, CD43 and Thy-1. A T cell receptor can be produced by expression of a naturally occurring gene encoding a T cell receptor and/or a heterologous nucleic acid molecule transformed into a cell. Similarly, an intracellular signal transduction molecule (e.g., PKCθ) as described herein can be produced in a cell by expression of a naturally occurring gene and/or by expression of a heterologous nucleic acid molecule transformed into the cell.

Preferably, a T cell for use in a method or assay of the present invention has a T cell receptor which binds to, or recognizes, an MHC-antigen complex on an antigen presenting cell. The MHC, or major histocompatibility complex, is a collection of genes encoding glycoproteins called major histocompatibility complex proteins. In vivo, the primary function of an MHC protein is to present antigen in a form capable of being recognized by a TCR. An MHC protein is bound to an antigen which is typically in the form of a peptide to form an MHC-antigen complex. As used herein, "MHC-antigen complex" refers to any MHC protein having an antigen bound to one or more of the MHC protein's antigen binding sites. As used herein, the term "antigen binding site" refers to the portion of an MHC protein capable of binding an antigen. Antigen binding sites can be internal binding sites (e.g., peptide binding grooves, such as those bound by antigenic peptides) or external binding sites (e.g., binding sites on the external surface of an MHC protein, such as those bound by superantigens). An antigen can include any antigen, and in particular, an antigenic peptide, that is capable of binding to an MHC protein in a manner such that the MHC-antigen complex can bind to TCR which recognizes that MHC-antigen complex, thereby effecting a T cell response.

As used herein, "T cell receptor recognition" refers to the ability of a T cell receptor (TCR) to bind to, or recognize, an MHC-antigen complex. The recognition of an MHC-antigen complex by a T cell normally leads to a T cell response that is antigen-specific (i.e., clone specific). Normal T cells are distinguished from T cell hybridomas which lose antigen specificity and may differ from normal T cells in their activation reactions and requirements. As used herein, "antigen presentation" refers to presenting antigen in such a manner that at least a portion of the antigen is available to be bound by a TCR. A T cell response occurs when a TCR recognizes an MHC protein bound to an antigen, thereby altering the activity of the T cell bearing the TCR. As used herein, a "T cell response" can refer to the activation, induction of anergy, or death of a T cell that occurs when the TCR of the T cell is bound by an MHC-antigen complex. As used herein, "activation" of a T cell refers to induction of signal transduction pathways in the T cell resulting in T cell proliferation, T cell differentiation, and/or production of cellular products (e.g., cytokines) by that T cell. The term, "T cell proliferation", refers to the clonal expansion of T cells that occurs as a result of antigen-specific T cell activation.

According to the above method of the present invention, T cells are cultured with antigen presenting cells (APCs) having MHC-antigen complexes, and it is determined whether activation of PKCθ occurs. Suitable APCs include, but are not limited to macrophages, dendritic cells and B cells (B lymphocytes). Suitable antigen presenting cells will stimulate (i.e., activate) a T cell if the T cell receptor recognizes the MHC-antigen complex (i.e., the T cell receives a first signal through the TCR-MHC-antigen binding), and if the appropriate costimulatory signals are delivered by the APC (i.e., the T cell receives a second signal through the interactions of other T cell-APC proteins). It is believed that signaling through the TCR alone is insufficient to optimally activate a T cell. As such, the absence of a second signal from a surface protein other than the TCR can result in T cell suppression which herein refers to one of the following: (1) failure to activate the T cell; (2) induction of a T cell into an anergic state; or (3) killing of the T cell. A variety of non-TCR proteins on the surface of a T cell can, in conjunction with MHC-antigen binding to TCR, mediate signal transduction resulting in T cell activation. Examples of such non-TCR proteins are listed above.

Treatment of T cells with anti-TCR/CD3 monoclonal antibodies induces cytokine production, but the cells later fail to proliferate and they undergo apoptosis. In addition, the present inventors have unexpectedly discovered that PKCθ is not translocated in antibody-activated T cells, demonstrating that non-antigen-specific stimulation of a variety of receptors on a T cell, even in combination, is not sufficient to activate PKCθ in the T cell. This finding, which is described in detail in the Examples section below, demonstrates that PKCθ participates in the induction of an antigen-specific T cell response. Therefore, without being bound by theory, the present inventors believe that PKCθ is involved in TCR-dependent proliferation, but not in triggering cytokine production.

In certain embodiments, a cell used in the methods and assays of the present invention is a genetically engineered cell, such as a cell that has been transformed with at least one heterologous nucleic acid sequence. Such a nucleic acid molecule can encode for a T cell receptor, for example, or for any molecules of a PKCθ signal transduction pathway, including PKCθ. A genetically engineered cell can include more than one heterologous nucleic acid sequence. A nucleic acid sequence, or molecule, as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a natural cell surface receptor gene such as regulatory regions that control production of a cell surface receptor encoded by that gene (such as, but not limited to, transcription, translation or posttranslation control regions) as well as the coding region itself.

A nucleic acid molecule can include functional equivalents of natural nucleic acid molecules encoding a protein or functional equivalents of natural nucleic acid sequences capable of being bound by proteins. Functional equivalents of natural nucleic acid molecules can include, but are not limited to, natural allelic variants and modified nucleic acid molecules in which nucleotides have been inserted, deleted, substituted, and/or inverted in such molecules without adversely affecting the function of products encoded by such sequences.

Transformation of a heterologous nucleic acid molecule (e.g., a heterologous cell surface receptor encoding nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of affecting either constitutive or regulated expression of the gene when the gene is transformed into a host cell. The phrase "recombinant molecule", as used herein refers to a gene operatively linked to at least one transcription control sequence on an expression vector. The phrase "expression vector", as used herein refers to a DNA or RNA vector that is capable of transforming a host cell, of replicating within the host cell, and of affecting expression of the operatively linked gene. Expression vectors are capable of replicating to either a high or low copy number depending on their inherent characteristics. Transcription control sequences, which can control the amount of protein produced, include sequences that control the initiation, elongation, and termination of transcription. Particularly important transcription control sequences are those which control transcription initiation, such as promoter and upstream activation sequences.

An expression system can be constructed from any of the foregoing control elements operatively linked to nucleic acid sequences using methods known to those of skill in the art. See, for example, Sambrook et al., 1989, Molecular Cloning: A Laboratory Manual, Cold Spring Harbor Labs Press, which is incorporated by reference herein in its entirety.

In assays of the present invention, T cells are cultured with antigen presenting cells under conditions (e.g., culture medium, temperature, oxygen, $CO_2$, incubation time) in which such cells can be maintained as viable cells and interact with other cells to activate signal transduction pathways. As such, the cells can be cultured in any suitable culture medium which contains components necessary for cell growth, such as assimilable carbon, nitrogen and micronutrients. Determination of suitable culture medium and growth conditions for such cells is well within the skill of the art.

As discussed above, regulation of PKCθ refers to any form of modulating PKCθ. More particularly, a characteristic of PKCθ activity can be assessed to determine whether PKCθ activity is regulated. Such characteristics of PKCθ activity include a change in the production of PKCθ, a change in the physical location of PKCθ from its location in a resting (i.e., non-activated) T cell (i.e., a translocation of PKCθ to the site of contact between a TCR and an MHC-antigen complex), and/or a change in the enzymatic activity of PKCθ. As such, up regulation, stimulation or activation of PKCθ can result in an increase in PKCθ production, a translocation of PKCθ from its location in a resting T cell, and/or an increase in PKCθ enzymatic activity. Similarly, a down regulation, or inhibition of PKCθ can result in a decrease in or inhibition of production of PKCθ, a lack of change in the physical location of PKCθ from its location in a resting (i.e., non-activated) T cell, and/or a decrease in or inhibition of the enzymatic activity of PKCθ.

The method of assessing or determining whether PKCθ is regulated in a T cell can be any detection method for evaluating the activation of PKCθ, such as any method for determining the translocation of PKCθ to the site of contact between the T cell and an APC, for determining a change in the level of PKCθ expression in the T cell, and/or for determining an increase in the level of enzymatic activity of PKCθ in the T cell. For example, the translocation of PKCθ in a cell can be evaluated by immunofluorescent microscopy. Such a method is described in detail in the Examples section herein. Other methods of determining whether PKC is activated in a T cell include in vitro kinase assays, which can measure the enzymatic activity of PKCθ in a cell (also described in detail in the Examples section) and transcription assays to detect the activation of PKCθ transcription, such as measuring the increase or decrease in mRNA transcription of PKCθ by PCR-based technology.

Another embodiment of the present invention includes a method to identify a regulatory compound which regulates T cell proliferation and regulatory compounds identified thereby. A method to identify a regulatory compound of the present invention comprises the steps of (a) culturing a T cell having a T cell receptor with an antigen presenting cell having an MHC-antigen complex such that the T cell receptor binds to the MHC-antigen complex to form an antigen-specific site of contact between the T cell and the antigen presenting cell; (b) contacting the T cell with a putative regulatory compound under conditions in which, in the absence of the putative regulatory compound, PKCθ is activated in the T cell; and (c) assessing the ability of the putative regulatory compound to regulate PKCθ in the T cell, wherein a change in a characteristic of PKCθ activity in the presence of the putative regulatory compound compared to in the absence of the putative regulatory compound indicates that the compound is able to regulate antigen-specific T cell proliferation. In one embodiment, the step of contacting a T cell with a putative regulatory compound is performed before the step of culturing the T cell with an antigen presenting cell. In another preferred embodiment, such a method is used to identify a regulatory compound that down regulates T cell proliferation. Modes of regulation of PKCθ and techniques for effecting such regulation have been previously discussed herein in detail. Similarly, suitable cells and culture conditions for the above method are essentially the same as those previously described herein for other assays and methods of the present invention.

As used herein, the term "putative" refers to compounds having an unknown signal transduction regulatory activity, at least with respect to the ability of such compounds to regulate T cell proliferation via the PKCθ signal transduction pathway. Putative regulatory compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, Molecular Biotechnology: Therapeutic Applications and Strategies, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as putative regulatory compounds by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

A regulatory compound of the present invention which regulates T cell proliferation is a compound that is capable of regulating a PKCθ signal transduction pathway, and in particular, PKCθ. Such a regulatory compound includes a compound that is capable of down regulating PKCθ, a compound that is capable of up regulating PKCθ, or a compound that is capable of preventing both the up regulation and the down regulation of the activity of PKCθ (i.e., maintaining or stabilizing the activity of a signal transduction pathway). Such regulation by a compound can be accomplished by, but is not limited to, any of the preferred methods of regulating PKCθ as described above (i.e. degrading a signal transduction molecule, etc.).

As discussed above, characteristics of PKCθ activity include a change in the production of PKCθ, a change in the physical location of PKCθ from its location in a resting (i.e., non-activated) T cell (i.e., a translocation of PKCθ to the site of contact between a TCR and an MHC-antigen complex), and/or a change in the enzymatic activity of PKCθ.

A suitable amount of putative regulatory compound(s) suspended in culture medium is added to the cells that is sufficient to regulate the activity of PKCθ such that the regulation is assessable using a detection method of the present invention as described previously. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with a signal transduction molecule. A preferred incubation time is between about 1 minute to about 12 hours. In one embodiment, a T cell is contacted with a putative regulatory compound prior to culturing the T cell with an antigen presenting cell. In another embodiment, the putative regulatory compound is added directly to the culture of T cells and antigen presenting cells.

The conditions under which a T cell of the present invention is contacted with, such as by mixing, a putative regulatory compound are conditions in which the cell can transduce a normal signal (i.e., activation of PKCθ) if essentially no regulatory compound is present. Such methods can include an effective medium in which the cell can be cultured such that the cell can exhibit signal transduction activity (i.e., activation of PKCθ), as described above. A preferred number of cells to use in the method of the present invention includes a number of cells that enables one to detect a change in PKCθ activity using a detection method of the present invention (as described above).

As used herein, an "effective amount" of a compound is at least the minimum amount of a compound that is necessary to minimally achieve, and more preferably, optimally achieve, the desired effect (i.e. regulation of PKCθ). An effective amount for use in a given method can be readily determined by one skilled in the art without undue experimentation, depending upon the particular circumstances encountered (e.g. concentrations, cell type and number, etc.).

A further embodiment of the present invention relates to a method to regulate T cell proliferation in a mammal in vivo by administering to a mammal a regulatory compound which regulates PKCθ. Another embodiment relates to a method to regulate T cell proliferation in a mammal by regulating PKCθ ex vivo. Ex vivo regulation can be accomplished by removing target cells (e.g., T cells) from a mammal, regulating such cells by an in vitro technique, and returning the cells to the mammal. Another embodiment relates to a method to down regulate, or suppress, T cell proliferation in a mammal in vivo by administering to a mammal a regulatory compound which inhibits PKCθ in the T cells of the mammal.

As used herein, in vivo delivery refers to the administration of a regulatory compound directly to an mammal. Ex vivo delivery of a regulatory compound refers to a method that includes the steps of contacting a population of cells removed from an mammal with a regulatory compound of the present invention under conditions such that the regulatory compound interacts with targeted cell types (i.e., T cells) and returning the contacted cells to the mammal. Methods to achieve such interaction include, but are not limited to, transfection, retroviral infection, electroporation, lipofection, bacterial transfer, spheroplast fusion, and adsorption.

The foregoing method can be used to treat mammals having a variety of diseases for which it is desirable to regulate T cell proliferation. Such diseases include, but are not limited to, an immunoproliferative disease, an autoimmune disease, graft-versus-host disease, an immunodeficiency disease, cancer, or an allergic disease. Similarly, the foregoing method can be used to down regulate T cell proliferation in a mammal which has received a transplant, such as an organ transplant or a bone marrow transplant. In a preferred embodiment, the foregoing method can be used to treat a mammal which has a disease or condition for which suppression (i.e., down regulation) of T cell proliferation may ameliorate the condition. Such diseases include, but are not limited to, an immunoproliferative disease, an autoimmune disease, graft-versus-host disease, or an allergic disease.

A regulatory compound to administer to a mammal to regulate (e.g., down regulate or up regulate) T cell proliferation includes any regulatory compound which regulates the activity of PKCθ as described above. Effective doses to administer to a mammal include doses administered over time that are capable of regulating T cell proliferation in the mammal. For example, a first effective dose can comprise an amount of a regulatory compound of the present invention that causes a minimal change in T cell proliferation when administered to a mammal. A second effective dose can comprise a greater amount of the same compound than the first dose. Effective doses can comprise increasing concentrations of the compound necessary to regulate T cell proliferation and ameliorate a disease involving such T cell proliferation in a mammal such that the mammal does not have an immune response to subsequent exposure to the compound. A suitable single dose of a regulatory compound of the present invention is a dose that is capable of substantially regulating T cell proliferation when administered one or more times over a suitable time period. A preferred single dose of a regulatory compound ranges from about 0.01 μg to about 1,000 milligrams (mg) of such a compound per subject, more preferred ranges being from about 0.1 μg to about 100 mg of a compound per subject, and even more preferred ranges being from about 1 μg to about 10 mg of a compound per subject.

A regulatory compound of the present invention can be administered to any mammal, preferably to humans. Acceptable protocols to administer a regulatory compound of the present invention in an effective manner include individual dose size, number of doses, frequency of dose administration, and mode of administration. Determination of such protocols can be accomplished by those skilled in the art depending upon a variety of variables, including the mammal to be treated and the stage of disease. Modes of delivery can include any method compatible with prophylaxis or treatment of a disease. Modes of delivery include, but are not limited to, parenteral, oral, intravenous, topical administration, local administration, and ex vivo administration to isolated T cells.

In one embodiment, a regulatory compound is administered to a mammal in conjunction with a pharmaceutically acceptable carrier. As used herein, a "pharmaceutically acceptable carrier" refers to any substance suitable as a vehicle for delivering a regulatory compound of the present invention to a suitable in vitro or in vivo site of action. Such a carrier is preferably able to deliver the regulatory compound to the T cells, and more preferably to a particular site, in a mammal. Preferred carriers are capable of maintaining regulatory compounds of the present invention in a form that is capable of regulating PKCθ in a T cell. Examples of such carriers include, but are not limited to water, phosphate buffered saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a recipient, for example, esters or partial esters of fatty acids containing from about six to about twenty-two carbon atoms. Examples of esters include, caproic, octanoic, lauric, palmitic, stearic, linoleic, linolenic, olesteric, and oleic acids. Formulations of the present invention can be sterilized by conventional methods and/or lyophilized.

Useful carriers for regulatory compounds of the present invention include any artificial or natural lipid-containing target molecule, preferably cells, cellular membranes, liposomes, and micelles. Preferably, formulations of the present invention are administered in the form of liposomes or micelles. Liposome and micelles of the present invention are capable of delivering a regulatory compound from the extracellular space of a cell to the intracellular space of a cell. Concentrations of a regulatory compound of the present invention combined with a liposome or a micelle include concentrations effective for delivering a sufficient amount of compounds of the present invention to a T cell such that regulation of PKCθ is effected. Such delivery systems are known and have been successfully applied in the art and are discussed in Maulik et al., ibid., which is incorporated by reference herein in its entirety.

Yet another embodiment of the present invention relates to a method to identify regulatory compounds which regulate PKCθ. Such a method comprises the steps of (a) contacting a cell which has a PKCθ signal transduction pathway with a putative regulatory compound and a stimulator, under conditions in which, in the absence of the putative regulatory compound, the stimulator initiates the PKCθ signal transduction pathway such that PKCθ is activated; and (b) assessing the ability of the putative regulatory compound to regulate the PKCθ signal transduction pathway in the cell, wherein a change in a characteristic of PKCθ activity in the cell in the presence of the putative regulatory compound compared to in the absence of the putative regulatory compound indicates that the compound is able to regulate PKCθ.

According to the present invention, a suitable cell for use in the above method to identify compounds which regulate PKCθ can be any cell which has a PKCθ signal transduction pathway which can be stimulated such that at least one characteristic of PKCθ activity, as described above, can be assessed. As such, a suitable cell for use in this method of the present invention includes genetically engineered cells, or recombinant cells. A preferred cell to use in such a method is a T cell, as previously described herein. Similarly, methods for assessing the ability of the putative regulatory compound to regulate the PKCθ signal transduction pathway in the cell have been previously described herein.

A "stimulator" to be used in the method above includes any compound or molecule which can either directly activate, or indirectly initiate activation of (e.g., by interaction with a receptor or molecule which in turn activates PKCθ signal transduction), a PKCθ signal transduction pathway, and in particular, PKCθ. As discussed above, a stimulator can be an exterior (i.e. acts outside of a cell) stimulator (e.g., an MHC-antigen complex on an antigen presenting cell) or an interior (e.g. acts inside the cell) stimulator. Examples of a suitable stimulator for use in the method above, include, but are not limited to, an APC having an MHC-antigen complex, an organic compound, a mitogen, and an antibody.

The following examples are provided for the purposes of illustration and are not intended to limit the scope of the present invention.

EXAMPLES

EXAMPLE 1

The following example demonstrates that only the PKCθ isoform clusters at (i.e., translocates to) the contact site of T cell-APC conjugates.

The cloned T cell line, D10.G4.1 (D10), is specific for the egg-white protein conalbumin and for $IA^k$ (MHC protein) and has been previously described. D10-IL2 is a subclone of D10. The B cell lymphoma CH12.LX (CH12) ($IA^k$) was used as an APC. The D10 cells were mixed at a 1:1 cell ratio with CH12 cells that were pulsed overnight with conalbumin (500 µg/ml). Cell conjugates were formed and processed. The affinity purified rabbit antibodies against the PKC isoforms α, β, δ, η, θ, and ζ (Santa Cruz Biotech, Inc., Santa Cruz, Calif.), were directed against unique peptide sequences at the C-terminal region of the proteins. Western blots with the anti-PKCθ antibody labeled a single band (≈80 Kd) in GP&E fibroblasts that were infected with a retroviral vector encoding for PKCθ and did not detect any protein bands in the parental uninfected cells. The ability of each of these antibodies to detect the specific PKC isoforms by immunofluorescence microscopy was confirmed by labeling, either in the presence or absence of PMA, a panel of fibroblast cell lines that overexpressed each of the PKC isoforms. The immunofluorescence and the corresponding Nomarski images of the cells were recorded by a chilled charge-coupled device digital camera (MCD1000, Spectra Source Inst., Westlake Village, Calif.) that was mounted on a Zeiss Axiophot microscope, equipped with a narrow-band optical fibers (Chromatech, Brattleboro, Vt.). The images were processed by a no-neighbor deconvolution program to remove out-of-focus haze. At least 400 cells were analyzed per coverslip.

Antigen-specific T cell-APC conjugates were formed by mixing the cloned D10 cells (T cells) with CH12 cells (APCs) that were pulsed with the antigen conalbumin. Each of the following PKC isoforms were labeled by immunofluorescence: α, β, δ, η, θ, and ζ. All of these PKC isoforms are expressed in lymphocytes and were detected by digital microscopic analysis of T cell-APC conjugates. The corresponding Nomarski images of the labeled cells were also created.

Surprisingly, only one of the PKC isoforms, PKCθ, was clustered at the cell membrane along the T cell-APC contact site. The labeling for each of the other PKC isoforms was distinctly punctuate and it remained similar in both bound (i.e., conjugated with an APC) and unbound T cells. No clustering of any of the other PKC isoforms was detected in D10-CH12 conjugates after either shorter or longer times of interaction.

In a separate experiment, the cells were labeled with either anti-PKCθ or anti-PKCδ. In this experiment, PKCθ was clustered in each of five D10-APC contacts, but was not clustered in the APC—APC contact (control). PKCθ was not clustered in any of four D10-APC contacts. In addition, there was no difference between the distribution of PKCδ in the APC-bound D10 cells (i.e., D10-APC conjugates) and the unbound D10 cell.

EXAMPLE 2

The following example demonstrates that the translocation of PKCθ to the site of T cell-APC contact was receptor-mediated and not a consequence of random cell—cell interactions.

The antigen-specificity of the PKCθ-translocation was tested in the following experiment. D10 cells were mixed with either untreated CH12 cells (i.e., not antigen pulsed) or CH12 cells that were pulsed with conalbumin. The cells were then doubly labeled with guinea pig anti-talin and affinity purified rabbit anti-PKCθ, and analyzed by digital microscopy. It is known that the clustering of talin, a cytoskeletal protein, at the T cell-APC cell contact indicates, at the single cell level, that the cells were activated. Within 10 minutes of cell mixing, the majority (70%) of T cells that were bound to antigen-pulsed CH12 cells and clustered talin, also displayed clustered PKCθ at the cell contact. The PKCθ translocation was persistent and by 55 minutes after cell mixing, PKCθ was clustered in essentially all (88%) of the cell conjugates. A three-dimensional quantitative analysis indicated that PKCθ clustered in the D10 cells and not in the CH12 cells. In the absence of antigen, fewer cell conjugates were formed, and none of them clustered PKCθ. In similar studies, cells were also labeled for the other PKC isoforms and again there was no difference in their distribution in either antigen-specific or nonspecific conjugates. The clustering of PKCθ was observed in each of eight other normal T cell clones and with primary lymph node T cell clones and with primary lymph node T cells from TCR-transgenic mice, which were activated by either antigen or superantigen. In contrast, the translocation of PKCθ was not seen in any of several antigen-specific T-cell hybridomas.

EXAMPLE 3

The following example demonstrates that PKCθ is enzymatically active in T cell-APC conjugates.

If PKCθ is involved in T cell activation, as would be predicted from its selective antigen-dependent translocation to the site of cell contact, it is likely to be enzymatically active in the T cell-APC conjugates. To measure its activity, PKCθ was immunoprecipitated from mixtures of D10 and CH12 cells, which were either untreated or pulsed with conalbumin. The immunoprecipitates were analyzed in an in vitro kinase assay using the Selectide peptide as a substrate.

Conjugates of D10 ($4 \times 10^6$ cells/assay) and CH12 ($2 \times 10^6$ cells/assay) were formed as described in Example 1 and 20 minutes later the cells were washed once in PBS and lysed (100 µl of 20 mM Tris, pH 7.5, and 0.5% NP-40, 0.25M NaCl, 3 mM EDTA, 3 mM EGTA, 1 mM PMSF, 2 mM $Na_3VO_6$, 20 µg/ml Aprotinin, 100 µg/ml Leupeptin, 1 mM DTT). After centrifugation, PKCθ and PKCδ were immunoprecipitated with the affinity purified rabbit antibodies (anti-PKCθ and anti-PKCδ) (1 µg) coupled to Protein A Sepharose beads. The beads were washed in PKC-kinase buffer (20 mM Hepes, pH 7.2, and 137 mM NaCl, 5.4 mM KCl, 0.3 mM $NaH_2PO_4$, 0.4 mM $KH_2PO4$, 25 mM β-glycerophosphate, 10 mm $MgCl_2$). The kinase assay was performed by the addition of 35 µl of kinase buffer containing 0.1 mM ATP, ($\gamma^{\pm\pm}P$)-ATP (20 µCi/assay) and 0.1 mM Selectide PKC substrate (CalBiochem, San Diego, Calif.) for 20 min. at 30° C. The reactions were stopped by the addition of 10 µl 25% TCA. The reaction mixtures were blotted on P81 phosphocellulose paper, washed with 75 mM phosphoric acid, to remove free ATP, dehydrated and counted in a scintillation counter (Beckman, Palo Alto, Calif.). For each set of conditions, reactions were also performed in the absence of the Selectide substrate. The level of phosphorylation of the substrate was determined by subtracting the radioactive counts that were obtained in the absence of the substrate from those obtained in its presence. In each case a parallel reaction mixture contained also 125 µg/ml of PMA, which causes maximal activation of the PKC that is present in the immunoprecipitate. Duplicate samples were analyzed for each assay.

The in vitro kinase activities of PKCθ from antigen-pulsed and unpulsed T cell-APC conjugates were strikingly different. PKCθ from the cell mixtures that were not pulsed with antigen was largely inactive. The addition of PMA in the assay caused a major increase (430%) in the phosphorylation of the substrate. In contrast, PKCθ from the antigen-pulsed cell mixtures was largely active, and the addition of PMA caused only a minor increase (13%) in the phosphorylation of the substrate. The similar activity of PKCθ, in the presence of added PMA, in the two immunoprecipitates indicated that the differences in the phosphorylation of the substrate reflect different states of activation and not simply quantitative differences in the amount of immunoprecipitated PKCθ. Indeed, Western blot analysis with anti-PKCθ antibodies of the Immunoprecipitates from the antigen-pulsed and unpulsed cell mixtures showed that essentially the same amounts of PKCθ were present in both immunoprecipitates. Since the microscopic observations indicated that a large fraction of cellular PKCθ became associated with the antigen-specific T cell-APC cell contacts, these findings show that the translocated PKCθ was enzymatically active.

Immunoprecipitates of another PKC isoform that did not translocate to the cell contact, PKCδ, which is the most homologous to PKCθ, were analyzed in parallel. The in vitro kinase activity of PKCδ, like its intracellular localization, was not affected by the interaction of the T cells with the antigen-pulsed APCs, and it remained largely inactive.

EXAMPLE 4

The following example demonstrates that PKCθ does not translocate and cluster with any of a variety of receptors when the T cell receptor stimulation is simulated by antibodies.

The selective TCR-dependent translocation of PKCθ to the membrane site where the T cell is bound to the APC suggests that PKCθ is associated with other proteins that cluster at this site. Such target proteins may be engaged-receptors, PKC-substrates or RACKs. The present inventors have previously demonstrated that in antigen-specific T cell-APC conjugates, the TCR, CD4 and LFA-1 cluster, along with the cytoskeletal protein talin, at the cell contact. Antibody-induced capping experiments demonstrated that the talin selectively associates with LFA-1 in activated T cells. To identify receptors with which PKCθ may be associated, the TCR/CD3, CD4, LFA-1 and CD28 were capped with specific monoclonal antibodies in the absence of APCs, and the localization of PKCθ was determined by digital microscopy. PKCθ did not colocalize with any of the capped receptors, including the capped TCR, regardless of the duration of the capping. Additional cocapping experiments with anti-CTLA-4, CD43, CD45 and Thy-1 also did not induce cocapping of PKCθ. Thus, while PKCθ translocates, like talin, to the cell-contacts during T cell-APC interactions, simulated activations with either individual or combinations of monoclonal antibodies failed to trigger a similar cocapping. The failure to cocap PKCθ with any of the tested receptors may be due to the association of the enzyme with yet another untested receptor. Without being bound by theory, the present inventors believe that, alternatively, the response of PKCθ may require a spatially and temporally coordinated set of multiple signals that can be provided only by properly engaged APCs.

EXAMPLE 5

The following example demonstrates that there is a tight coupling between the induction of MTOC-reorientation/cell proliferation and PKCθ translocation.

To determine the role of PKCθ in T-cell activation, the responses of T cells which were activated under conditions that either cause or fail to cause the translocation of PKCθ were tested. The cloned D10-IL2 cells were mixed with CH12 cells that were pulsed with either high (500 µg/ml) or low (0.5 µg/ml) concentration of the antigen conalbumin. The cells were triply labeled with anti-PKCθ, anti-talin and anti-tubulin, to visualize the microtubule-organizing center (MTOC). The present inventors have previously shown that activation of T cells by APCs which were pulsed with optimal concentrations of antigen causes both talin clustering and MTOC reorientation, and results in T cell proliferation. In contrast, activation of T cells by APCs which were pulsed with suboptimal concentrations of the same antigen is sufficient to induce talin-clustering but does not result in MTOC-reorientation and cell-proliferation. Microscopic analysis of the D10-IL2-CH12 conjugates demonstrated that in essentially all of the cell-conjugates formed in the presence of high concentrations of antigen, both talin and the MTOC were rearranged towards the contact area, and in these cells PKCθ was clustered at the contact area. In contrast, in the cell conjugates that were formed in the presence of low concentration of antigen, talin did cluster at the contact area, but the MTOC remained randomly oriented, and PKCθ was not clustered at the contact area. In additional dose-response experiments, the APCs were pulsed with intermediate concentrations of antigen. The numbers of cells with reoriented-MTOCs and clustered PKCθ decreased with less antigen. Most significantly, over the entire range of antigen-concentrations, all T cells with clustered PKCθ (>99%) had their MTOCs reoriented toward the bound APCs. These experiments indicate a tight coupling between the induction of MTOC-reorientation/cell proliferation and PKCθ translocation.

EXAMPLE 6

The following example further demonstrates that induction of PKCθ and cell proliferation are tightly coupled cellular events.

A similar correlation between the induction of PKCθ translocation and cell proliferation was observed when we compared the responses of T cells to APCs that were pulsed with agonist and altered peptides. The cloned T cell line, AK8, is specific for the antigen conalbumin and Ia$^k$, like the D10 cell line. The sequence of the conalbumin peptide that AK8 cells recognize as antigen is HRGAIEWEGIESG (CA132–144) represented herein as SEQ ID NO:1. The addition of CA132–144 (1 µg/ml) to AK8 cells in the presence of irradiated APCs caused extensive T cell proliferation, as measured by thymidine incorporation. In contrast, the peptide CA132–144/R133H (CA2), which includes a single amino-acid substitution in position 2 of CA132–144, inhibited the CA132–144-induced proliferation of AK8 cells in a dose dependent manner. Microscopic observations showed that in essentially all of the AK8-CH12 conjugates that were pulsed with the CA132–144 peptide, both talin (85% ±1.2%) of the cells) and PKCθ (85% ±10% of the cells) were clustered at the cell contact area. In contrast, in cell conjugates that were pulsed with CA132–144 and CA2, conditions that result in extensive inhibition (~80%) of cell proliferation, talin was enriched in essentially all of the conjugates (88% ±4%), but PKCθ clustered only in a minority of the conjugates (18% ±6%). The pulsing of the APCs with only CA2, which does not induce detectable proliferation of AK8 cells, resulted in the formation of significantly less T cell-APC conjugates (about 20% of control levels). Talin was still clustered in most (70% ±1.5%) of these conjugates, indicating some activation, but PKCθ clustering was almost never (2% ±1%) observed in these conjugates.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:

1. An assay for evaluating the ability of a T cell to proliferate in response to an antigen-specific stimulus, comprising:
   (a) culturing a T cell, having a T cell receptor, with an antigen presenting cell, having an MHC-antigen complex comprising an MHC protein and an antigen, wherein said antigen is bound to an antigen binding site of said MHC protein; and
   (b) determining whether protein kinase C theta (PKCθ) is selectively activated in said T cell such that PKCθ, and no other of six known isoforms of PKC in T cells, translocates to a site of contact between said T cell and said antigen presenting cell.

2. The assay of claim 1, wherein said step of determining comprises a technique selected from the group consisting of determining an increase in the level of PKCθ expression compared to the level of PKCθ in a resting T cell, determining whether PKCθ translocates to the site of contact between said T cell receptor and said MHC-antigen complex, and determining whether PKCθ is enzymatically active.

3. The assay of claim 1, wherein said step of determining comprises using immunofluorescent microscopy to determine whether PKCθ translocates to the site of contact between said T cell receptor and said MHC-antigen complex.

4. The assay of claim 1, wherein said step of determining comprises using a kinase assay to determine whether PKCθ is enzymatically active.

5. The assay of claim 1, wherein said T cell is selected from the group consisting of a primary lymph node T cell, a primary splenic T cell and a T cell from a transgenic mouse.

6. The assay of claim 1, wherein said T cell is a T cell clone.

7. A method to identify a regulatory compound which regulates T cell proliferation, comprising:
   (a) culturing a T cell, having a T cell receptor, with an antigen presenting cell, having an MHC-antigen complex comprising an MHC protein and an antigen, wherein said antigen is bound to an antigen binding site of said MHC protein, and wherein said T cell receptor binds to said MHC-antigen complex to form an antigen-specific site of contact between said T cell and said antigen presenting cell;
   (b) contacting said T cell with a putative regulatory compound under conditions in which, in the absence of said putative regulatory compound, protein kinase C theta (PKCθ), and no other of six known isoforms of PKC in T cells, translocates to said site of contact in said T cell; and
   (c) assessing the ability of said putative regulatory compound to regulate PKCθ in said T cell, wherein a change in a characteristic of PKCθ activity in the presence of said putative regulatory compound compared to in the absence of said putative regulatory compound indicates that said compound is able to regulate antigen-specific T cell proliferation.

8. The method of claim 7, wherein said step of contacting said T cell with a putative regulatory compound is performed before said step of culturing said T cell with said antigen presenting cell.

9. The method of claim 7, wherein said step of assessing comprises determining the ability of said putative regulatory compound to down regulate PKCθ.

10. The method of claim 7, wherein said change in the characteristic of PKCθ activity comprises a characteristic selected from the group consisting of an change in the level of PKCθ production, a translocation of PKCθ to said site of contact between said T cell and said antigen presenting cell, and a change in the level of enzymatic activity of said PKCθ.

11. The method of claim 7, wherein said step of assessing is performed by immunofluorescent microscopy.

12. A method to identify a regulatory compound which regulates protein kinase C theta (PKCθ), comprising:

a) contacting a cell, having a PKCθ signal transduction pathway, with a putative regulatory compound and a stimulator, under conditions in which, in the absence of said putative regulatory compound, said stimulator selectively initiates said PKCθ signal transduction pathway such that PKCθ, and no other of six known isoforms of PKC in T cells, translocates to a site of contact between said cell and said stimulator;

b) assessing the ability of said putative regulatory compound to regulate said PKCθ signal transduction pathway, wherein a change in a characteristic of PKCθ activity in said cell in the presence of said putative regulatory compound compared to in the absence of said putative regulatory compound indicates that said compound is able to regulate PKCθ.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Gallus gallus

<400> SEQUENCE: 1

His Arg Gly Ala Ile Glu Trp Glu Gly Ile Glu Ser Gly
1               5                   10